United States Patent [19]

Barry et al.

[11] Patent Number: 5,055,306

[45] Date of Patent: Oct. 8, 1991

[54] SUSTAINED-RELEASE FORMULATIONS

[75] Inventors: Brian W. Barry, Leeds; Bryan A. Mulley, Bradford; Peter York, Ilkley, all of United Kingdom

[73] Assignee: APS Research Limited, Cleckheaton, United Kingdom

[21] Appl. No.: 260,415

[22] Filed: Oct. 20, 1988

[30] Foreign Application Priority Data

Oct. 22, 1987 [GB] United Kingdom ............... 8724763

[51] Int. Cl.$^5$ .................... A61K 9/32; A61K 9/46; A61K 9/36
[52] U.S. Cl. .................... 424/482; 424/466; 424/480
[58] Field of Search .................... 424/466, 480, 482

[56] References Cited

U.S. PATENT DOCUMENTS

| 3,131,123 | 4/1964 | Masquelier | 424/466 |
| 3,961,041 | 6/1976 | Nishimura et al. | 424/466 |
| 4,147,768 | 4/1979 | Shaffer et al. | 44/466 |
| 4,348,091 | 3/1984 | Gruber et al. | 424/480 X |
| 4,765,988 | 8/1988 | Sonobe et al. | 424/480 |
| 4,786,505 | 11/1988 | Lovgren et al. | 424/480 X |
| 4,832,956 | 5/1989 | Gergely et al. | 424/466 |
| 4,844,905 | 7/1989 | Ichikawa et al. | 424/466 X |

FOREIGN PATENT DOCUMENTS

| 0052076 | 11/1980 | European Pat. Off. |
| 0207041 | 6/1986 | European Pat. Off. |
| 0255404 | 7/1987 | European Pat. Off. |
| 2086725 | 11/1981 | United Kingdom |

OTHER PUBLICATIONS

"Eudragit® NE30D" Technical Application Pamphlet, Aqueous Dispersion for Controlled-Release Permeable Film Coatings.

Primary Examiner—Thurman K. Page
Assistant Examiner—Amy Hulina
Attorney, Agent, or Firm—Spencer & Frank

[57] ABSTRACT

A granular sustained-release formulation of a pharmacologically active substance presented in the form of a tablet, said tablet comprising sufficient granules to provide a predetermined dose or number of doses of the pharmacologically active substance and effervescent or water-dispersible ingredients, each of said granules having a diameter of preferably between 0.5 and 2.5 mm and comprising:

a) a core comprising one or more pharmacologically active substances and preferably one or more excipients; and b) a coating covering substantially the whole surface of the core and comprising 100 parts of a water insoluble but water swellable acrylic polymer and from 20 to 70 parts of a water soluble hydroxylated cellulose derivative, the weight of the coating being from 2 to 25% of the weight of the core.

A method for preparing this effervescent of water-dispersible tablet formulation is also provided. Such formulations enable large dosages in sustained-release form to be more easily administered to patients.

9 Claims, 9 Drawing Sheets

SUSTAINED-RELEASE FORMULATIONS

FIELD OF THE INVENTION

This invention relates to granular sustained-release pharmaceutical formulations presented in the form of effervescent or water-dispersible tablets. The tablets enable large dosages to be more easily administered to patients. A method for preparing such sustained-release formulations is also provided.

Some medical conditions are best treated by administration of a pharmaceutical which is formulated to allow the active substance or ingredient to act as quickly as possible. Such a formulation may comprise an injectable solution or a readily dissolvable tablet or capsule. This type of formulation is useful, for instance, for treating acute pain, such as headaches, or pain associated with sudden trauma, such as an accident.

Other medical conditions are best treated by administration of a pharmaceutial in such a way as to sustain its action over an extended period of time. This type of administration is useful, for example, for treating chronic pain, such as that associated with rheumatic or arthritic conditions. It can be achieved by repeated administration of an immediate-release tablet or capsule at frequent intervals, for instance every four hours. However, this is generally inconvenient, especially during the night, when it is often necessary to awaken a patient to administer the tablet or capsule. In addition, such multiple dosing may lead to undesirable fluctuations in the plasma concentration of the active substance.

It has previously been proposed to produce a formulation which will release the active substance therein at a controlled rate such that the amount available in the body to treat the condition is maintained at a relatively constant level over an extended period of time. Particularly suitable periods are twelve or twenty-four hours, since such formulations need only be taken twice or once a day to maintain an effective treatment of the condition. Such formulations are generally known as "sustained-release formulations."

Granular sustained-release formulations are conventionally presented to patients in the form of capsules, for instance gelatin capsules, containing an amount of granules sufficient to deliver a predetermined dosage of the pharmacologically active ingredient over a predetermined period of time. Alternatively, the granules may be formed into traditional tablets and presented to the patient in this way. Tablets of such formulations are often accompanied by instructions that they should be swallowed whole and not broken up in the mouth.

Many pharmacologically active substances have to be taken by patients in relatively large doses, for example unit doses of 200–500 mg at a frequency of 3 or 4 times per day are not uncommon. Unfortunately, conventional sustained-release formulations designed to provide the patient with such dosages and containing a sufficient amount of the pharmacologically active ingredient that they need to be taken perhaps once every twelve or even twenty-four hours, whether presented as capsules or as traditional tablets, are too large for reasonable patient acceptability and compliance. Young children and elderly people, in particular, have difficulty in swallowing large capsules and tablets. With some formulations, this problem can be reduced by splitting the dosage into several smaller capsules or tablets. The patient then has to remember to take more than one of the capsules or tablets and this can also present problems. Furthermore, some patients have difficulty in swallowing any size of solid dosage form. This is particularly the case, for example, with patients suffering from certain forms of cancer.

GB 2166651 A refers to a controlled-release powder comprising microparticles with an average size of from 0.1 to 125 $\mu$m, each of the microparticles being in the form of a micromatrix of an active ingredient uniformly distributed in at least one non-toxic polymer. Various ways of presenting the powder are mentioned and these include encapsulation into gelatin capsules and formulation into ointments or suspensions. There is also a brief reference to the possible formulation of effervescent tablets. However, the disclosure is concerned solely with powders of uncoated microparticles and it will be appreciated that microparticles are more difficult and costly to handle during processing than are granules of larger diameter. In addition, it is difficult, and depending upon size sometimes impossible, to apply a regular coating to each microparticle and so formulations of such powders are not suitable for use in all types of sustained-release compositions.

GB 2087235 A describes a granular sustained-release formulation and refers to the possibility of tabletting the granules. U.S. Pat. No. 4,728,513 also relates to a granular delayed-release formulation, the granules most preferably having a diameter of 0.3 to 0.5 mm, and which is said to be an improvement on the formulation of GB 2087235 A. This U.S. patent again refers to the possible tabletting of the granules, but specifies the need for the dry coated granules to be heated for at least 5 minutes at a temperature of from 5° to 120° C. This heat treatment is said to be essential in order to obtain various improved properties in the sustained-release formulations of the patent, but it obviously represents an additional process step (and additional expense) and is thus a disadvantage. A further consideration is that some drugs do not tolerate exposure to high temperatures even for short times without adverse consequences; certain drugs, for example ibuprofen, have melting points well below 120° C. and chemical breakdown often occurs on heating, which adversely affects the stability of the product. Both GB 2087235A and U.S. Pat. No. 4,728,513 clearly state that the resulting tablets disintegrate into separate granules in the stomach or gastrointestinal tract. There is no suggestion of presenting the formulations in the form of effervescent or water-dispersible tablets.

Effervescent and water-dispersible tablets are, of course, well known. A review of such tablets appears in The Pharmaceutical Journal, Mar. 12, 1983, p289–294, F. E. J. Sendall et al. It is believed, however, that it has not previously been suggested that granular sustained-release formulations could be successfully presented in the form of effervescent or water-dispersible tablets.

The present invention is based on the discovery of ways of presenting pharmacologically active substances in a sustained-release form which overcomes the aforementioned difficulties associated with conventional sustained-release formulations. In particular, the formulations of the present invention enable large dosages in sustained-release form to be more easily administered to, and swallowed by, the patient.

BRIEF DESCRIPTION OF THE DRAWINGS

The figures illustrate dissolution profiles of various tablet formulations.

DETAILED DESCRIPTION OF THE INVENTION

Figure 1:
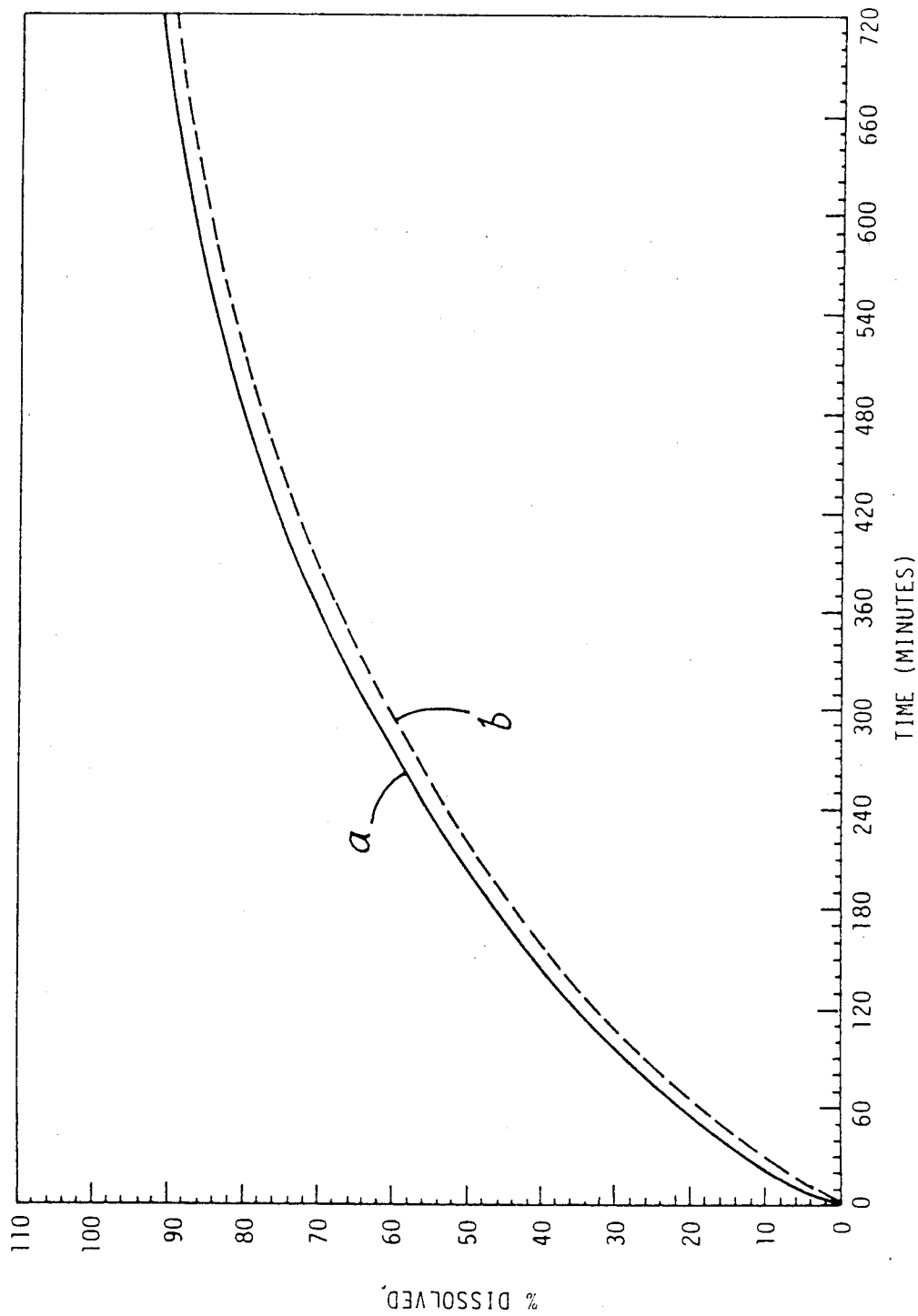
FIG. 1 illustrates dissolution curves for Ibuprofen beads (a) and Ibuprofen sustained-release effervescent tablets (b)

According to the present invention there is provided a granular sustained-release formulation of a pharmacologically active substance presented in the form of a tablet, said tablet comprising sufficient granules to provide a predetermined dose or number of doses of the pharmacologically active substance and effervescent or water-dispersible ingredients, each of said granules preferably having a diameter of between 0.5 and 2.5 mm and comprising:

a) a core comprising one or more pharmacologically active substances and preferably one or more excipients; and b) a coating covering substantially the whole surface of the core and comprising 100 parts of a water insoluble but water swellable acrylic polymer and from 20 to 70 parts of a water soluble hydroxylated cellulose derivative, the weight of the coating being from 2 to 25% of the weight of the core.

The invention further provides a method for preparing a sustained-release formulation in the form of an effervescent or water-dispersible tablet and which comprises:

i) mixing one or more pharmacologically active substances with preferably one or more excipients;

ii) forming the mixture into core particles;

iii) forming a suspension comprising 100 parts of a water insoluble but water swellable acrylic polymer and from 20 to 70 parts of a water soluble hydroxylated cellulose derivative;

iv) coating the said core particles with the said suspension to form granules having a diameter of preferably between 0.5 and 2.5 mm, the weight of the coating being from 2 to 25% of the weight of the core; and v) compressing a sufficient amount of the granules to provide a predetermined dose or number of doses of the pharmacologically active substance, together with effervescent or water-dispersible ingredients, so as to form a tablet.

The formulations of this invention are thus presented in the form of tablets which disintegrate into sustained-release granules upon coming into contact with an aqueous liquid. The tablets are prepared by compacting the granules using traditional compression methods and machinery.

In all tabletting processes external mechanical forces are applied to powder masses to produce coherent compacts with mechanical strength. Conventionally, the powder mass consists primarily of specially prepared granules, which are agglomerates of powders, together with a small percentage of fine powder, often referred to as 'fines'. As the forces are applied, following rearrangement and repacking of particles at low loads, granule and powder particle deformation occur as the load is increased to normal tabletting forces. A review of this topic appears in The Theory and Practice of Industrial Pharmacy: Lachman, L., Lieberman, H. A. and Kanig, J. L., 3rd Edition, Lea and Febiger, Philadelphia, 1986, p.72-79. It is well recognised that the principle mechanisms which lead to particle bonding and tablet formation are brittle fracture and plastic deformation. These mechanisms cause granule and particle breakage and permanent deformation. This may also be accompanied by the generation of new surfaces by the breakage and formation of bonds between particles. Granule and particle fracture on compression has been demonstrated by, for example, increases in specific surface area of powdered materials on compression. This was referred to by, for example, Higuchi, T., Rao, A. N., Busse, L. W. and Swintosky, J. V.; J. Am. Pharm. As. Sci. Ed., 42:194 (1953). The presence of newly generated and clean surfaces, brought into close proximity through the applied force, is thought to lead to particle bonding and thereby create mechanical strength in the formed tablet.

Since granular and powdered materials are crushed and deformed on tabletting, the accepted teaching clearly indicates that thin polymeric film coatings applied to the surfaces of granules and powders should be similarly broken and deformed on compression. If the film coatings are designed to control the rate of drug release, then it follows that the controlling effect will either be lost or rendered ineffective. It has surprisingly been found that compression of the granular formulation of the present invention into tablet form does not significantly damage or destroy its structure, and in particular the coating on the granules remains substantially intact, and thus the sustained-release characteristics of the granules are not impaired. Indeed, it has further been discovered that by varying the compression force applied during the manufacture of the tablets, the release characteristics of the granules can be altered in a reproducible manner. It is generally found that there is a complex relationship between the compression force and the subsequent release of the active ingredient, as illustrated in Examples 5 and 7, and this is presumably the result of some limited deformation of the coating. It is believed that these surprising and advantageous findings are largely attributable to the combination, and amounts, of materials used in the coating of the granules.

It is believed that sustained-release formulations of pharmacologically active substances have not previously been presented, or at least successfully presented, in the form of effervescent or water-dispersible tablets. The formulations of the present invention enable large dosages to be more easily swallowed by the patient than previously known formulations and it is envisaged that they will find wide applicability. The invention will now be described in more detail.

Considering firstly the effervescent tablet, its manufacture involves compressing granules containing the pharmacologically active substance with substances which effervesce upon coming into contact with an aqueous liquid, for example sodium bicarbonate with a suitable organic acid. A patient would be able to place such a tablet in his or her mouth and the tablet would immediately begin to effervesce due to the patient's salivation process. Of course, the process of salivation can be assisted by the intake of water, if required. Alternatively, an effervescent tablet could be added to water or other liquid whereupon the effervescent ingredients in the tablet dissolve to leave an aqueous dispersion or suspension of the granular sustained-release formulation and which can then be swallowed easily by the patient.

Turning now to the water-dispersible tablet, its manufacture would involve compressing the granules containing the pharmacologically active substance with one or more substances which are water-dispersible. Such a tablet would be added to water to give a dispersion or suspension of the granular sustained-release formulation in the water and which can then be swallowed easily by the patient. Alternatively, a patient would be able to place such a tablet in his or her mouth and the tablet would immediately begin to disperse due to the patient's salivation process. Of course, the process of salivation can be assisted by the intake of water. It is to be understood that the term "water-dispersible" as used herein is intended to also refer to other non-toxic aqueous liquids as well as water.

If desired, the tablets of the present invention may also contain suspending agents, surfactants, lubricants, flavouring agents, sweetening agents and/or colouring agents. These are conventional materials which may be incorporated in conventional amounts.

It has been found that following the disintegration in water of the effervescent or water-dispersible tablets of this invention, the granules can remain in suspension for a considerable time without significant loss or escape of the pharmacologically active substance. Such suspensions could be prepared by a doctor or pharmacist, for example, and then stored for a period of days or weeks before being administered to a patient. The suspension might also be flavoured to mask the unpleasant taste of many pharmacological substances. It is to be understood that suspensions formed from the effervescent or water-dispersible tablets are within the scope of this patent.

It will be appreciated that to a large extent the diameter of the granules, and the composition and amount of coating will depend on the time over which the formulation is designed to work and the nature of the particular pharmacologically active substance concerned. Generally, however, each of the granules will have a diameter of between 0.5 and 2.5 mm, most preferably between 0.7 and 1.2 mm.

Typically, for a formulation in which the granules provide sustained-release over a period of 12 hours, the diameter of the granules will be between 0.7 and 1.2 mm, the coating contains from 20 to 70 parts of the water soluble hydroxylated cellulose derivative, and the weight of the coating is between 2 and 15% of the weight of the core.

For a formulation in which the granules provide sustained-release over a period of 24 hours, typically the diameter of the granules will be between 0.7 and 1.2 mm, the coating contains from 20 to 70 parts of the water soluble hydroxylated cellulose derivative, and the weight of the coating is between 5 and 25% of the weight of the core.

In addition to the pharmacologically active substance, the granules may contain one or more excipients and these could include, for example: polyvinyl pyrrolidone, methyl cellulose, hydroxypropylmethyl cellulose, mannitol, citric acid, glycerol, propylene glycol, polyethylene glycol and carbomer. Many other excipients are conventionally included in sustained-release formulations and these are well known to those skilled in the art.

The granules may contain a bulking agent such as microcrystalline cellulose. This is a well known form of cellulose which is partially depolymerised. A particularly suitable microcrystalline cellulose is sold under the name Avicel (a registered trade mark). However, other conventional bulking agents may also be used, as will be readily apparent to those skilled in the art. The granules may further contain a diluent, such as lactose. A channelling or capillary-active agent, such as sodium carboxymethylcellulose, which is sold under the name Ac-Di-Sol (a registered trade mark), may additionally be included. These components are used in conventional amounts.

The granules used in the formulation of this invention have a coating which comprises a water insoluble but water swellable acrylic polymer and a water soluble hydroxylated cellulose derivative. Suitably, for every 100 parts of the water insoluble but water swellable acrylic polymer present in the coating, there will be from 20 to 70 parts of the water soluble hydroxylated cellulose derivative. The weight of the coating will usually be from 2 to 25% of the weight of the granule. As is also well known in the art, however, the precise composition and nature of the coating will vary according to the type of pharmacologically active substance involved, the time over which the sustained-release formulation is desired to act and the part of the gastrointestinal tract where release from the granules is required.

The coating most preferably comprises about 30 parts of the hydroxylated cellulose derivative. If too much is present, the coating may become too sticky and the rate of release may become too high. If too little is present, the rate of release may be too low. A particularly suitable hydroxylated cellulose derivative is hydroxypropylmethyl cellulose having a degree of substitution of 28 to 30% of methoxy groups and 7 to 12% of hydroxy groups. However, other equivalent materials such as hydroxypropyl, hydroxyethyl or hydroxymethyl celluloses can be used.

The acrylic polymer component of the coating is preferably neutral and may comprise a homopolymer or a copolymer, for instance of acrylic acid esters or methacrylic acid esters. Preferably, the acrylic polymer is provided as an aqueous dispersion. A particularly suitable acrylic polymer is sold under the name Eudragit (a registered trade mark), which comprises a copolymer of acrylic and methacrylic acid esters and which is usually supplied as an aqueous dispersion containing approximately 30% solids. Most preferably, the polymer used is Eudragit NE30D.

As a means of presenting pharmacologically active substances in an easily swallowed sustained-release form, the present invention is of general applicability. For instance, examples of pharmacologically active substances that can be used in the sustained-release formulations of the present invention include: drugs acting on the gastrointestinal system (such as cimetidine), the cardiovascular system (such as anti-arrythmics e.g. verapamil; beta-adrenoceptor blockers e.g. propranolol, atenolol; anti-hypertensives e.g. methyldopa, levodopa and prazosin; vasodilators e.g. verapamil, nifedipine, nicardipine, diltiazem; antiplatelets e.g. dipyridamole), drugs acting on the respiratory system (such as bronchodilators e.g. salbutamol, theophylline; antihistamines e.g. pheniramine maleate) and the central nervous system (such as anti-psychotics e.g. flupenthixol, lithium salts; appetite suppressants e.g. fenfluramine; antinauseants e.g. hyoscine, metoclopramide; analgesics e.g. paracetamol, dextropropoxyphene, narcotic analgesics; nonsteroidal antiinflammatory drugs e.g. ibuprofen, flurbiprofen, naproxen, mefenamic acid, ketoprofen, indomethacin, indoprofen, azapropazone, dicclofenac, difluisal, fenbufen, fenoprofen, piroxicam, sulindac, suprofen, tiaprofenic acid, tolmetin, droxicam, meloxicam, tenoxicam, etodolac, oxindanac; antiepileptics e.g. sodium valproate; antiparkinsonism drugs e.g. benzhexol, levodopa), antiinfectives (such as antibiotics e.g. erythromycin, tetracycline, the penicillins and cephalosporins; antituberculous drugs; antileprotics; and other antimicrobial drugs; antifungal drugs, antiviral drugs e.g. acyclovir; antiprotozoal drugs; antimalarial drugs), drugs acting on the endocrine system (such as drugs used in diabetes e.g. tolbutamide, metformin; sex hormones e.g. oestradiol) and the urinary tract (such as bethanecol, phenylpropanolamine), drugs affecting nutrition and the blood (such as iron preparations, vitamins and electrolytes), drugs administered to treat musculoskeletal and joint diseases (such as analgesics, antiinflammatory and nonsteroidal antiinflammatory drugs as detailed previously; sulphasalazine, probenecid) and neuromuscular disease (such as neostigmine), skeletal muscle relaxants (such as orphenadrine, dantrolene) and drugs acting at the eye (such as acetazolamide).

It is believed that many pharmacologically active substances or mixtures of two or more of such substances can be formulated in a sustained-release form according to the present invention. The invention is particularly, though not exclusively, useful for preparing sustained-release formulations of drugs which are administered in high dosages. Obviously the amount of pharmacologically active substance contained in each of the granules, together with the other excipients, will depend on the predetermined dosage of that substance that it is intended to provide to the patient. Different drugs, of course, have different dosages and the recommended dosages for particular drugs are known by those skilled in the art. The amount of pharmacologically active substance to be used in the granules can, as is known from conventional sustained-release formulations be predetermined having regard to the final dose to be taken by a patient. Sustained-release formulations according to the present invention can thus be designed to deliver specific doses of a particular pharmacologically active substance over a predetermined period of time.

Conventional (i.e. non-sustained-release) effervescent and water-dispersible tablets are, of course, well known and it is not necessary to describe their preparation in detail. As will be appreciated, effervescent tablets contain functional constituents which react together in the presence of water to generate a gas. Thus, a base constituent, generally a bicarbonate or carbonate, reacts with an acid constituent, generally an organic carboxylic acid, to generate, most usually, carbon dioxide. Suitable acid constituents include citric acid, tartaric acid, malic acid, fumaric acid, adipic acid, succinic acid, and ascorbic acid; acid anhydrides such as succinic anhydride and citric anhydride, and acid salts such as sodium dihydrogen phosphate, disodium dihydrogen pyrophosphate, sodium acid suphite, monopotassium citrate, potassium acid tartrate and sodium fumarate. Suitable carbonate sources include sodium bicarbonate, sodium carbonate, potassium bicarbonate, potassium carbonate, sodium sesquicarbonate, sodium glycine carbonate, calcium bicarbonate, calcium carbonate and magnesium carbonate. In the case of water-dispersible tablets, a soluble component is required to bulk the tablet weight, to facilitate disintegration and to provide acceptable taste. Suitable materials include mannitol, lactose, sucrose, dextrose, xylitol, sorbitol and fructose.

The formulations of this invention might typically be prepared in the following manner. If necessary, the pharmacologically active substance is micronised so as to increase its surface area and thereby improve dissolution. It is then blended with one or more conventional excipients, such as a bulking agent, a diluent and a channelling or capillary-active agent. The blending is conveniently performed by mixing the components together with some water to produce a slightly cohesive product. This is then extruded, chopped into suitable lengths, spheronised and dried to form the granules of the formulation. The coating is prepared by forming a solution of, for example, a water soluble hydroxylated cellulose derivative and mixing it with a dispersion of a water insoluble but water swellable acrylic polymer. The aqueous mixture is then used to coat the dried granules, and the coated granules are subsequently dried. Preferably, the coated granules are then sieved to ensure that they are in the correct size range.

The resulting granules are then compounded with effervescent or water-dispersible substances into tablets which disintegrate upon coming into contact with an aqueous liquid. Other conventional additives, such as lubricants, surfactants and flavouring agents, may of course also be included in the tablets.

The present invention provides sustained-release formulations presented in forms which enable large dosages to be more easily administered to, and swallowed by, the patient. It is believed that, using this invention, many known pharmacological compositions can now be presented to the patient in these more acceptable forms. Accordingly, it is to be understood that the aforementioned pharmacologically active substances and excipients serve only to illustrate possible formulations for use with the present invention. Other materials conventionally used in sustained-release formulations which will be well known to those skilled in the art, could be used in the formulations of this invention. It will be appreciated that the term "granules" as used herein is intended to also cover other similar particles which might, in conventional sustained-release formulations, normally be referred to as beads or pellets, etc.

The present invention will now be illustrated by the following Examples. The Examples are by way of illustration; they do not necessarily represent fully optimised formulations. The formulations described below were developed using the OSAT system developed by the inventors at the University of Bradford. Dissolution tests were performed on the resulting formulations and the dissolution profiles obtained are shown in the accompanying FIGS. 1 to 9.

EXAMPLE 1

A sustained-release formulation according to the present invention was prepared in the form of an effervescent tablet in the following manner:

(a) Manufacture of Granules

| | |
|---|---|
| Ibuprofen B.P. | 4.000 Kg |
| Microcrystalline cellulose U.S.N.F. | 0.800 Kg |
| Water | 2.7 Liters |

The ibuprofen and the microcrystalline cellulose were mixed together in a dry blender. Water was added in portions until a slightly cohesive product was formed. The cohesive product was passed through an extruder (Alexanderwerk Extruder with a 1.0 mm cylinder) and the extruded material was chopped to produce slugs having a diameter of about 1 mm and a length of 2 to 3 mm. The slugs were spheronised by passage through a spheroniser, (G. B. Caleva Spheroniser), and the granules thus formed were dried to constant weight.

Preparation of Coating

| | |
|---|---|
| Eudragit NE30D | 1.4 Kg |
| Hydroxypropylmethylcellulose | 0.13 Kg |
| Water | 1.2 Kg |

The hydroxypropylmethyl cellulose was dissolved in the water and mixed with the Eudragit.

Coating of the Granules

The granules were rotated in a 16" copper coating pan and the coating mixture was added in portions to the pan until a loading of 10-13% w/w (based on the dried, initial granule weight) was achieved.

(b) Preparation of Effervescent Base

| | |
|---|---|
| Citric acid in fine powder | 180 g |
| Tartaric acid in fine powder | 270 g |
| Sodium bicarbonate | 510 g |
| Sucrose | 150 g |

The ingredients were mixed, heated to form a cohesive mass and granules were produced by forcing through a sieve.

(c) Tablet Formulation

Tablets of 10 mm in diameter were formed from a mixture of the granules containing ibuprofen (400 mg equivalent to 300 mg of ibuprofen) and those of the effervescent base (300 mg) under a range of compressional loads and these were found to have crushing strengths of between 1 and 20 Kg. Disintegration measurements gave times of from 9-300 seconds or more. Tablets of adequate appearance and with crushing strengths of between 4 and 6.9 Kg and disintegration times between 36 and 70 seconds were selected for dissolution studies.

In this, and the subsequent Examples, the following techniques were used to measure crushing strength, disintegration and dissolution:

Crushing Strength Test—A tester Model 2E/205, Series 7211 made by Heberlein and Co. A. G., Zurich was used.

Disintegration Test—A tablet was placed in 50 ml of water at 20° C. contained in a flat-bottomed 200 ml glass beaker and gently swirled. The time taken for the tablet to form discrete granules (or beads) following effervescence (or disintegration in the case of the subsequently exemplified water-dispersible tablets) was taken as the disintegration time.

Dissolution Test—U.S.P. paddle method, pH 6.8, flat-bottomed flask, temperature of 37° C., detector wavelength 224 nm, optical density of a 300 mg/l ibuprofen solution=1.3011.

d) Results

Dissolution tests were performed on samples of the effervescent tablets of the present invention having a crushing strength of 4.8 Kg. For comparative purposes, tests were also performed on samples of the granules (or beads) containing ibuprofen which were not compounded into tablets. The results are shown in FIG. 1. The dissolution profiles for the effervescent tablets and the loose granules are almost identical and this shows that compacting the granules into tablets has not damaged their structure (in particular their coating). The sustained-release properties of the granules are thus maintained in the effervescent tablet formulation. Similar results were obtained for other tablets with crushing strengths of between 4 and 6.9 Kg.

(e) Human acceptability trials

For human acceptability trials larger tablets (20 mm in diameter, 2.0 g) were prepared from a mixture of placebo coated granules (800 mg equivalent to 600 mg ibuprofen), granules of the effervescent base (800 mg) and orange flavouring powder (400 mg; Apeel, Birds Ltd.).

The tablets were administered to six subjects with instructions to suck and then swallow material released from the tablet. Subjects were asked to report on the ease and acceptability of taking the product. All reported that the tablets fizzed pleasantly in the mouth, that the gas released and the taste of the product induced salivation with consequent easy swallowing of the disintegrating mass. There were no problems with retention of granules or excipient material in the mouth.

EXAMPLE 2

A sustained-release formulation according to the present invention in the form of a water-dispersible tablet containing granules of ibuprofen (of the type prepared in Example 1), was prepared in the following manner:

(a) Mannitol Base

| | |
|---|---|
| Mannitol | 79.59% |
| Avicel 101 | 7.25% |
| Polyvinyl Pyrrolidone | 9.0% |
| Gelatin | 1.16% |

| | |
|---|---|
| -continued | |
| Water | 6.0% |

The ingredients were mixed together to form a mass and granules were produced by subsequent sieving and drying.

(b) Tablet Formation

The Mannitol granules (800 mg) and coated granules containing ibuprofen according to Example 1, (800 mg), either with or without a flavouring agent (400 mg or 600 mg; Apeel, Birds Ltd.), were compacted to form tablets (20 mm in diameter) at pressures of 3500–3700 lb per square inch. Tablets with crushing strengths of 2.5 to 2.9 Kg and disintegration times of between 32 and 43 seconds were produced.

These tablets dispersed in the mouth and were best administered with a draught of water. Dissolution characteristics of the tablets were similar to those shown in FIG. 1.

EXAMPLE 3

A sustained-release formulation according to the present invention was prepared in the form of an effervescent tablet in the following manner:

(a) Manufacture of Granules

| | |
|---|---|
| Nifedipine U.S.P. | 21 g |
| Carbomer | 42 g |
| Microcrystalline cellulose U.S.N.F. | 237 g |
| Hydrochloric acid 0.1M | 90 ml |

The nifedipine and the carbomer were mixed together by the doubling up technique in a dry blender. Microcrystalline cellulose was then added, again using the doubling up technique. Hydrochloric acid was added in portions until a slightly cohesive product was formed. The cohesive product was passed through an extruder (Alexanderwerk Extruder with 1.0 mm cylinder) and the extruded material was chopped to produce slugs having a diameter of about 1 mm and a length of 2 to 3 mm. The slugs were spheronised by passage through a spheroniser, (G. B. Caleva Spheroniser), and the granules thus formed were dried to constant weight.

Preparation of Coating Formulation

| | |
|---|---|
| Eudragit NE30D | 100 g |
| Hydroxypropyl methylcellulose | 9 g |
| Water | 86 g |

The hydroxypropyl methylcellulose was dissolved in the water and mixed with the Eudragit.

Coating of the Granules

The granules were rotated in a 6" copper coating pan and the coating mixture was added in portions to the pan until a loading of 10% w/w (based on the dried, initial granule weight) was achieved.

(b) Preparation of Effervescent Base

As for Example 1.

(c) Tablet Formulation

Tablets of 13 mm in diameter were formed from a mixture of the granules containing nifedipine (316 mg equivalent to 20 mg of nifedipine) and those of the effervescent base (316 mg) under a range of compressional loads.

Crushing strength test—As for Example 1.
Disintegration test—As for Example 1.
Dissolution test—B.P. basket method, pH 6.8, flat-bottomed flask, temperature of 37° C., detector wavelength 238 nm, optical density of a 3 mg/l nifedipine solution=$0.169_5$. As the solubility of nifedipine in buffer at 37° C. is 11 mg/l it was necessary to break the tablets into pieces, a dissolution test was carried out on each piece, the results being added together to give a dissolution profile for the whole tablet.

(d) Results

Figure 2:
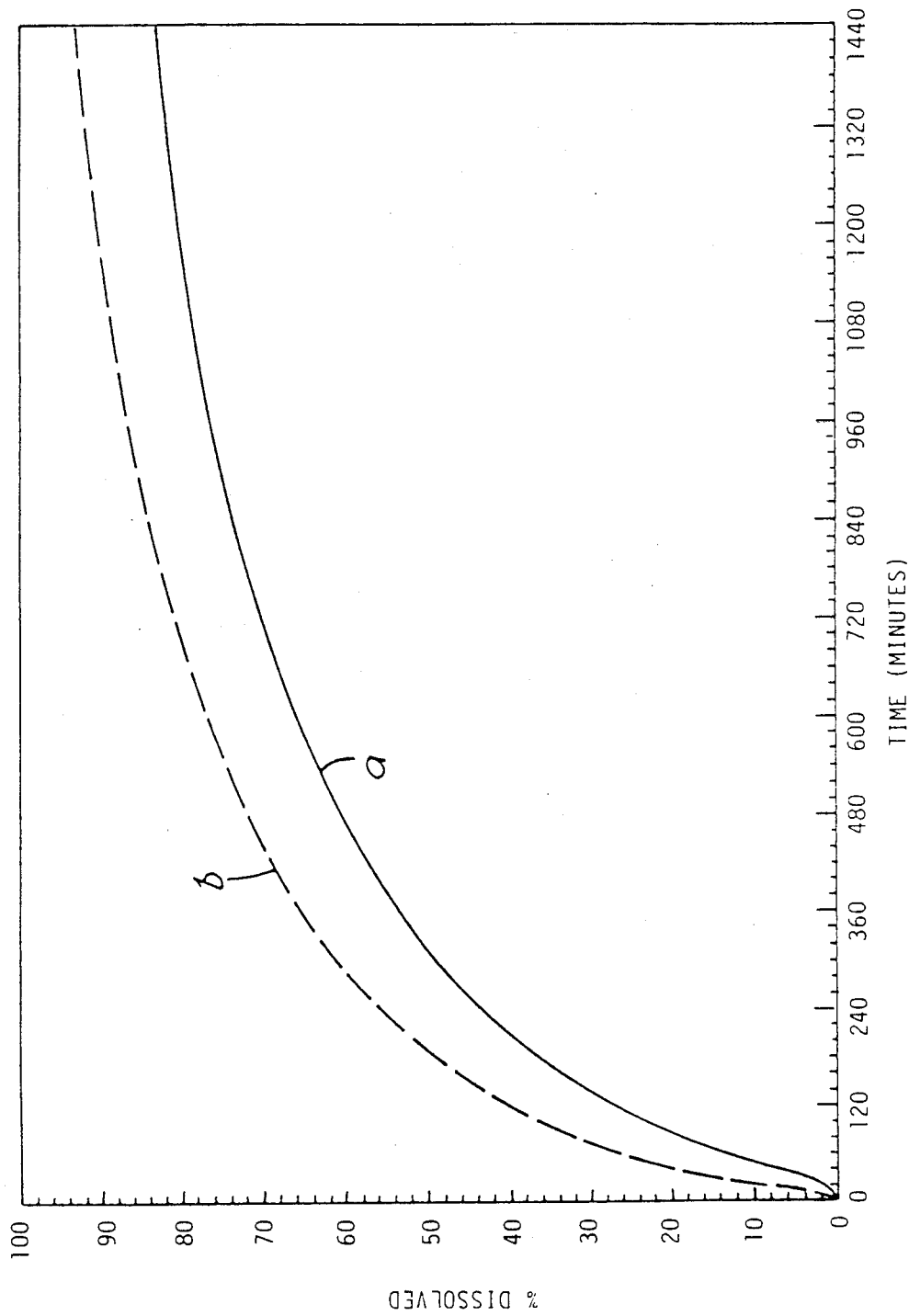
FIG. 2 illustrates dissolution curves for Nifedipine beads (a) and Nifedipine sustained-release effervescent tablets (b)

Dissolution tests were performed on samples of the effervescent tablets of the present invention (having a crushing strength of 6 Kg). For comparative purposes, tests were also performed on samples of the granules containing nifedipine which were not compounded into tablets. The results are shown in FIG. 2. The dissolution profile for the effervescent tablet shows a slightly faster release of nifedipine than for the loose granules. This indicates that there has been some modification of the granule coat during effervescent tablet formation. However, the changes are not sufficient to destroy the sustained-release properties of the granules. By adjusting the coating loading of the granules, manufacture of sustained-release effervescent nifedipine tablets with required release profiles could be achieved. Note that all operations involving nifedipine were performed in subdued light.

EXAMPLE 4

A sustained-release formulation according to the present invention in the form of a water dispersible tablet was prepared in the following manner:

(a) Mannitol Base

As for Example 2.

(b) Tablet Formation

The Mannitol granules (316 mg) and coated granules containing nifedipine according to Example 3, (316 mg), were compacted to form tablets (13 mm in diameter) under a range of compressional loads.

Crushing strength test—As for Example 1.
Disintegration test—As for Example 1.
Dissolution test—As for example 3.

Figure 3:
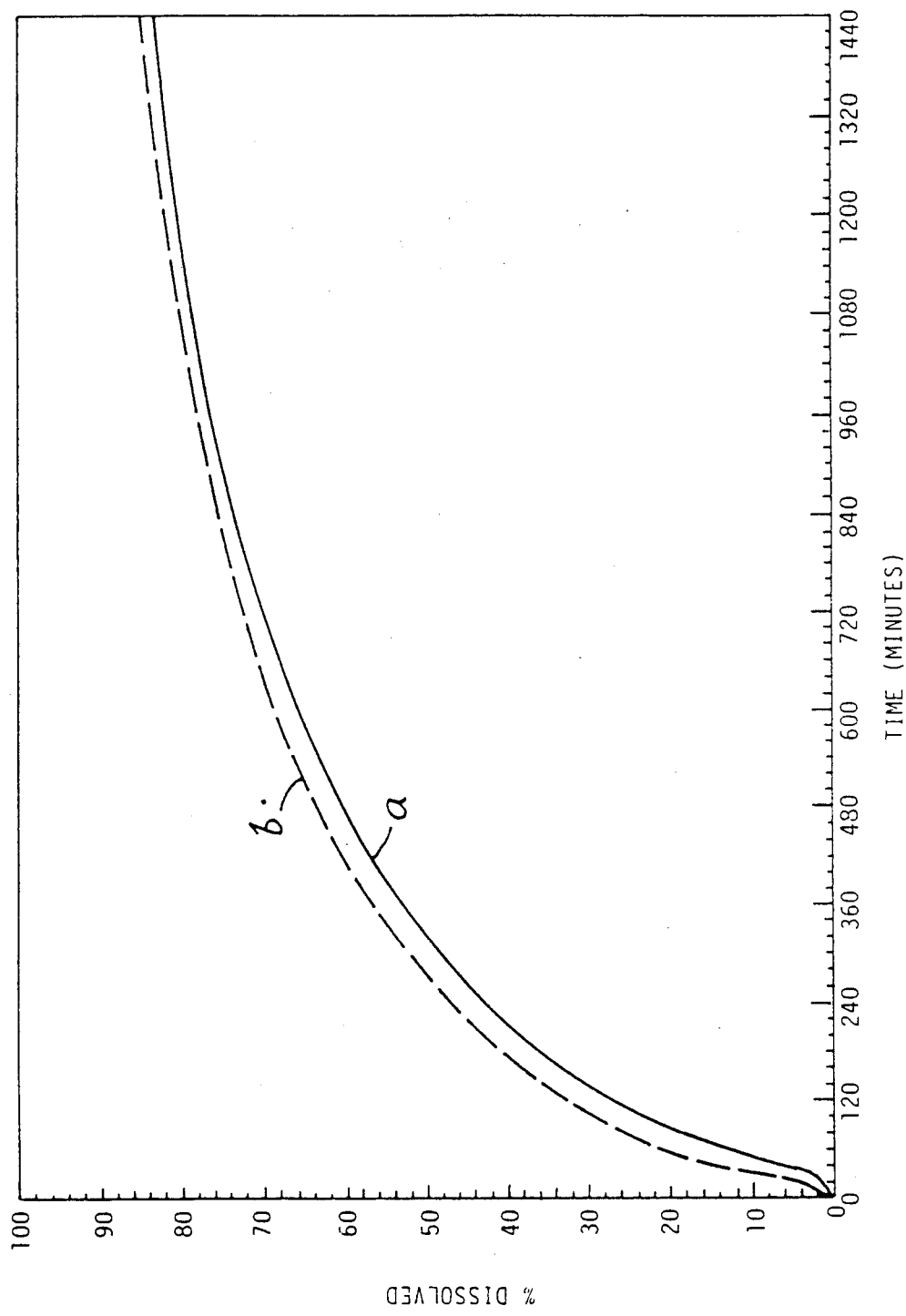
FIG. 3 illustrates dissolution curves for Nifedipine beads (a) and Nifedipine sustained-release dispersible tablets (b)

Tablets with crushing strengths of 5 Kg and disintegration times between 120 and 180 seconds were examined. The dissolution profiles for the dispersible tablets and the loose granules are almost identical (FIG. 3). This shows that compacting the granules into dispersible tablets has not damaged their structure (in particular their coating). The sustained-release properties of the granules are thus maintained in the dispersible tablet formulation.

Note that all operations involving nifedipine were performed in subdued light.

EXAMPLE 5

A sustained-release formulation according to the present invention was prepared in the form of an effervescent tablet in the following manner:-

(a) Manufacture of Granules

| | |
|---|---|
| Naproxen B.P. | 1.000 Kg |
| Microcrystalline Cellulose U.S.N.F. | 0.200 Kg |
| Water | 0.440 Liters |

The naproxen and the microcrystalline cellulose were mixed together in a dry blender. Water was added in portions until a slightly cohesive product was formed. The cohesive product was passed through an extruder (G. B. Caleva with 1.0 mm cylinder) and the extruded material was chopped to produce slugs having a diameter of about 1.0 mm and a length of about 2 to 3 mm. The slugs were spheronised by passage through a spheroniser G. B. Caleva Spheroniser) and the granules thus formed were dried to constant weight.

Preparation of Coating

| | |
|---|---|
| Eudragit NE30D | 76.92 g |
| Hydroxypropyl methylcellulose | 6.92 g |
| Water | 66.16 ml |

The hydroxypropyl methylcellulose was dissolved in the water, and mixed with the Eudragit.

Coating of the Granules

Two batches were prepared to produce a 2% w/w and 3% w/w coating level (based on the dried initial granule weight). The naproxen granules were rotated in a 16" copper coating pan and the coating mixture was added in portions to the pan until a loading of 2% w/w or 3% w/w was achieved.

(b) Preparation of Effervescent Base

The effervescent base was prepared as in Example 1, except the granules were formed by use of the Extruder and Spheroniser rather than a sieve.

(c) Tablet Formulation

Tablets with a bevelled edge and 12.7 mm diameter were formed from a mixture of the granules containing naproxen and those of the effervescent base in a 1:1 ratio with 0.5% w/w magnesium stearate as lubricant. Tablets were prepared for each of the batches of 2% and 3% coated granules at three different compaction pressures, these giving crushing strengths of approximately 1.0, 5.0 and 9.0 Kg respectively and disintegration times of between 90 and 200 seconds. Tablets containing 525 mg of naproxen granules (equivalent to 435 mg naproxen) and 525 mg of the effervescent base granules were used for dissolution studies.

Crushing Strength—As for Example 1.
Disintegration Test—As for Example 1.
Dissolution Test—U.S.P. method using baskets, media-pH 6.8, flat-bottomed flasks, temperature of 37° C., detector wavelength 262 nm, optical density of a 500 mg/l naproxen solution=1.103.

(d) Results

Figure 4:
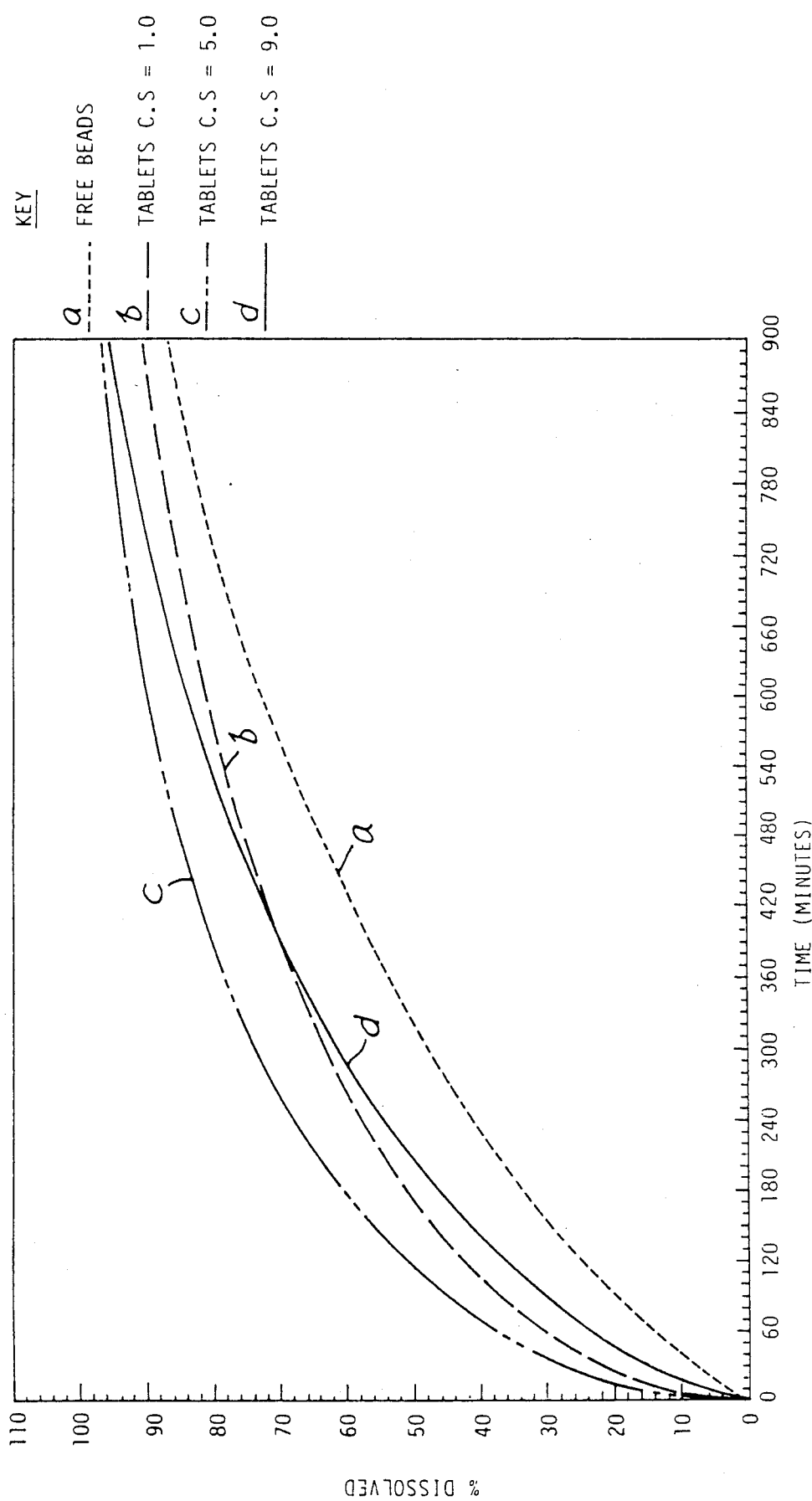
FIG. 4 illustrates dissolution test on 2% coated Naproxen beads as free beads (a) and as effervescent tablets formed at three compaction pressures (b:c:d)
Figure 5:
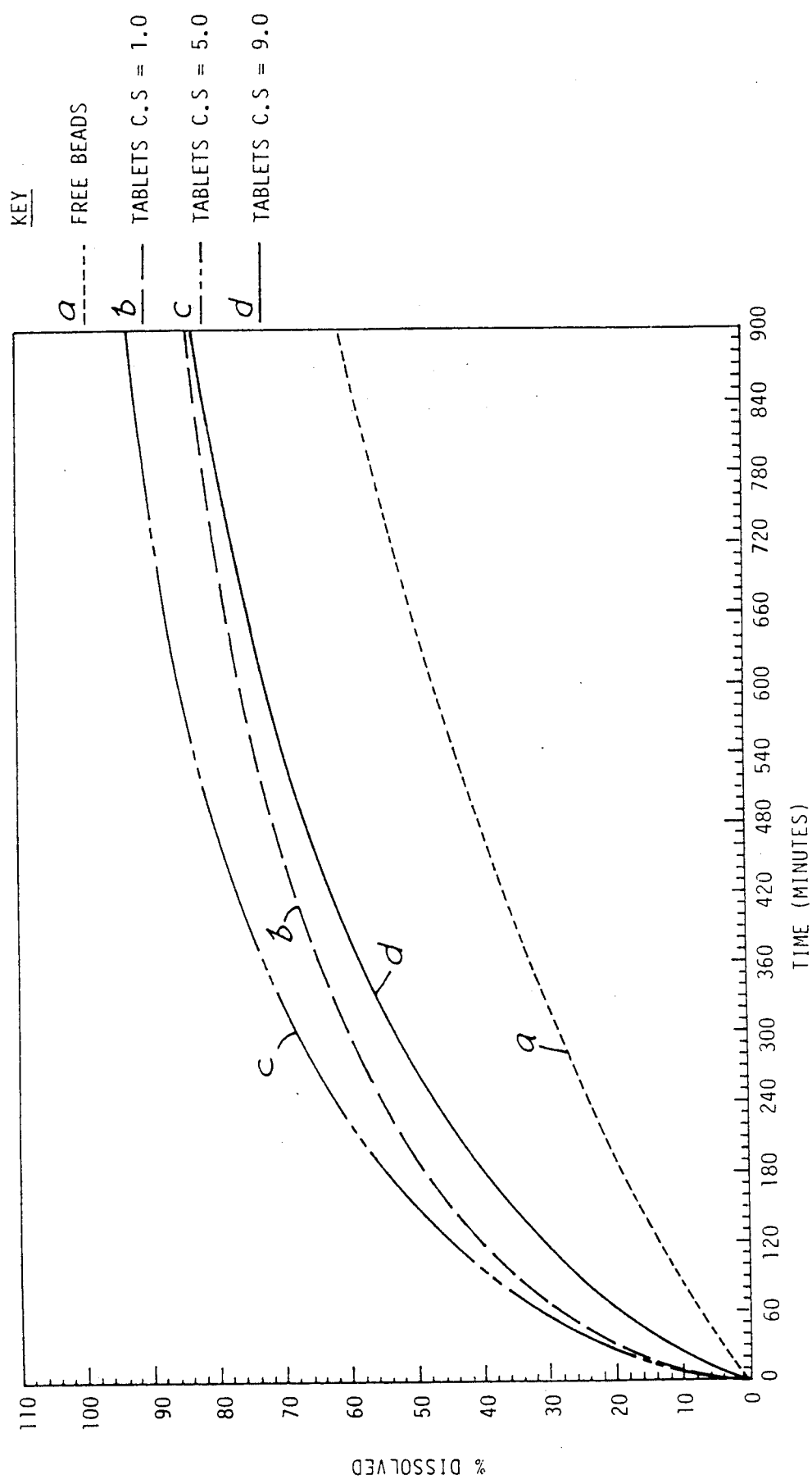
FIG. 5 illustrates dissolution tests on 3% coated Naproxen beads as free beads (a) and as effervescent tablets formed at three compaction pressures (b:c:d)

Dissolution tests were performed on samples of the effervescent tablets of the present invention (having crushing strengths (C.S.) of between 1.0 Kg and 9.0 Kg). For comparative purposes, tests were also performed on samples of the granules containing naproxen which were not compounded into tablets. The results are shown in FIGS. 4 and 5. The dissolution profiles for the effervescent tablets show a faster release than for the loose granules, at both coating levels. However, the changes are not sufficient to destroy the sustained-release properties of the granules.

Thus, it is possible to obtain a suitable dissolution profile for the effervescent tablet by using granules with slightly increased coating levels compared to the loose granules. The release profile thus obtained falls well within the desired specifications.

The effect of different compaction pressures can also be seen in FIGS. 4 and 5. An increase in pressure to produce tablets of crushing strength of 5.0 Kg, from the minimum required to form a tablet of crushing strength 1.0 Kg, causes an increase in the release of the drug, for both 2% and 3% coated beads. Higher pressure (producing tablets of crushing strength 9.0 Kg) slows the release down for at least the first six hours of dissolution. Thus the profile required can also be achieved by controlling the compaction pressure as well as by the level of coating on the beads.

EXAMPLE 6

A sustained-release formulation according to the present invention in the form of a water-dispersible tablet was prepared in the following manner:

(a) Mannitol Base

As for Example 2.

(b) Tablet Formation

The mannitol granules (618 mg) and 3% w/w coated granules containing naproxen according to Example 5 (618 mg)—equivalent to 500 mg naproxen—were compacted to form tablets of 20 mm diameter at a pressure of 3000 lbs/sq. inch.

Crushing strength test—As for Example 1.
Disintegration time—As for Example 1.
Dissolution test—As for Example 5.

(c) Results

Figure 6:
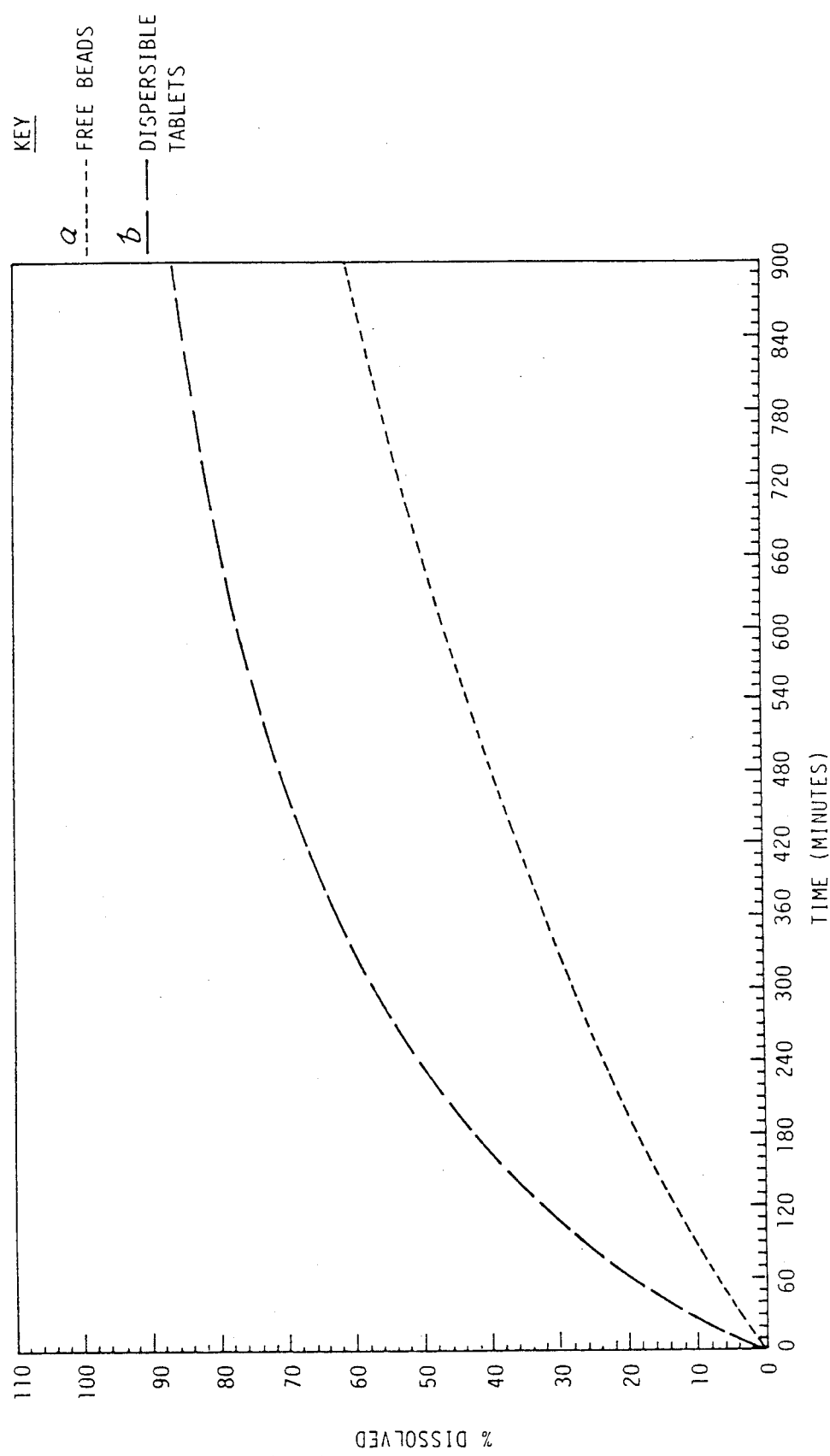
FIG. 6 illustrates dissolution tests on 3% coated Naproxen beads as free beads (a) and as dispersible tablets (b)

Tablets with a crushing strength of about 5.3 kg and disintegration times of between 150 and 180 seconds were used for dissolution study. The dissolution profile obtained for the dispersible tablet containing naproxen granules showed faster drug release compared to the free beads. As for the effervescent tablet, it would appear that whilst the granule structure is modified on compaction, suitable sustained-release profiles complying with required specifications can be obtained. The results are shown in FIG. 6.

EXAMPLE 7

A sustained-release formulation according to the present invention was prepared in the form of an effervescent tablet in the following manner:

(a) Manufacture of Granules

| | |
|---|---|
| Mefenamic acid B.P. | 240 g |
| Tween 80 (4% solution) | 60 ml |
| Microcrystalline cellulose U.S.N.F. | 57.4 g |
| Water | 55 ml |

The mefenamic acid was placed in a blender bowl and agitated whilst the Tween 80 solution was added. When well mixed, the microcrystalline cellulose was added, followed by portions of water until a slightly cohesive product was produced. This product was passed through an extruder (Alexanderwerk Extruder with 1.0 mm cylinder) and the extruded material was chopped to produce slugs having a diameter of about 1 mm length of 2 to 3 mm. The slugs were spheronised by passage through a spheroniser (G. B. Caleva Spheroniser), and the granules thus formed were dried to constant weight.

Preparation of Coating

| | |
|---|---|
| Eudragit NE30D | 25.64 g |
| Hydroxypropyl methylcellulose | 2.31 g |
| Water | 22.05 ml |

The hydroxypropyl methylcellulose was dissolved in the water and mixed with the Eudragit.

Coating of the Granules

The granules were rotated in a 6" copper coating pan and the coating mixture was added in portions to the pan until a loading of 3% w/w (based on the dried, initial granule weight) was achieved.

(b) Preparation of the Effervescent Base

As for Example 1.

(c) Tablet Formulation

Tablets of 9 mm in diameter were formed from a mixture of the granules containing mefenamic acid (103 mg equivalent to 80 mg of mefenamic acid) and those of the effervescent base (206 mg). Additional tablets were prepared at different compaction pressures, these giving crushing strengths of approximately 1, 4 and 8 Kg.

Crushing strength test—As for Example 1.

Dissolution test—In this Example, and in Example 8, the dissolution test employed followed the U.S.P. basket method with the following conditions:

pH 7.4, round bottomed flasks, temperature of 37° C., detector wavelength 286 nm, optical density of an 80 mg/L mefenamic acid solution=3.141.

(d) Results

Figure 7:
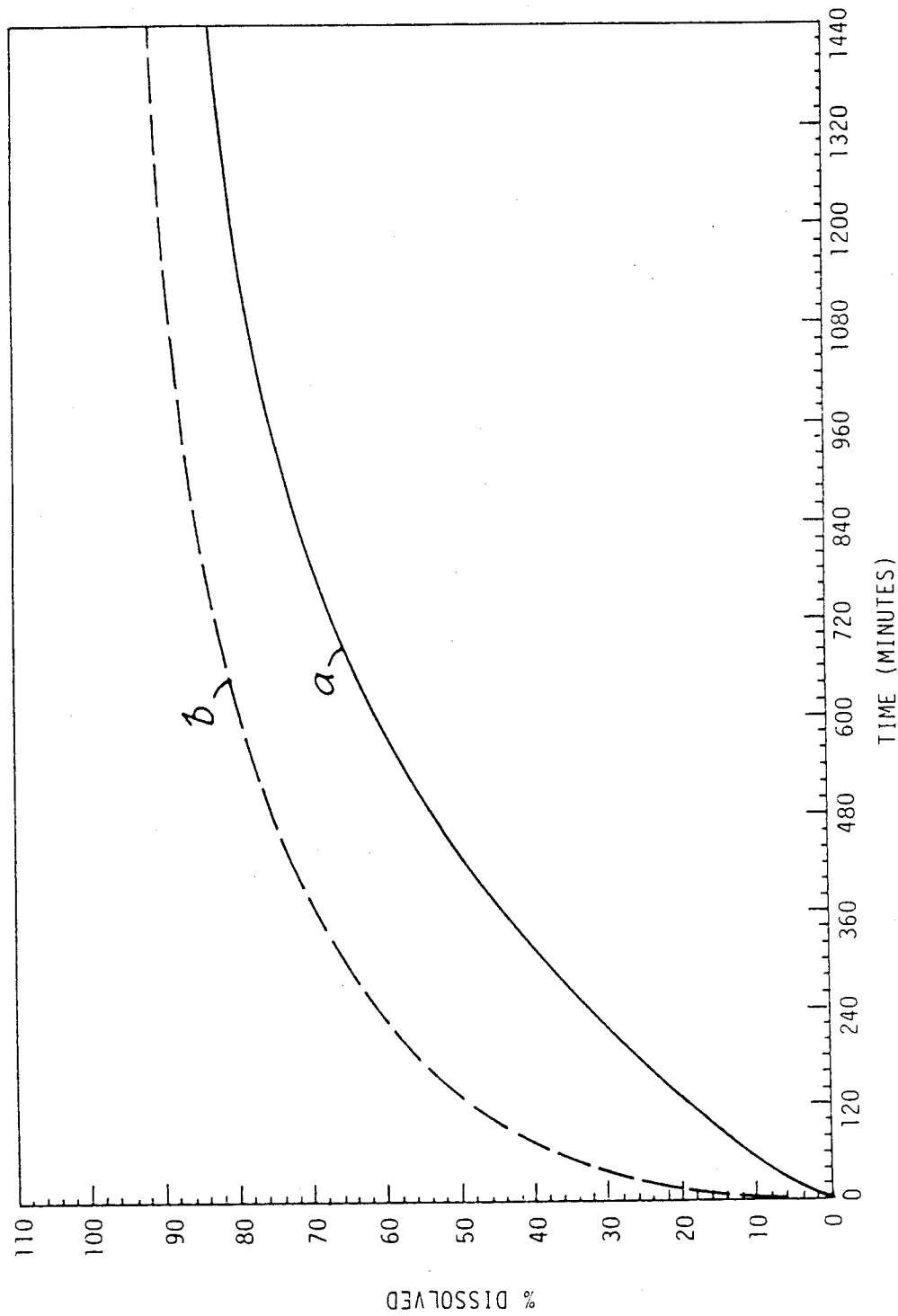
FIG. 7 illustrates comparison of the dissolution profiles of 3% coated Mefenamic acid beads free (a) and tabletted (b)
Figure 8:
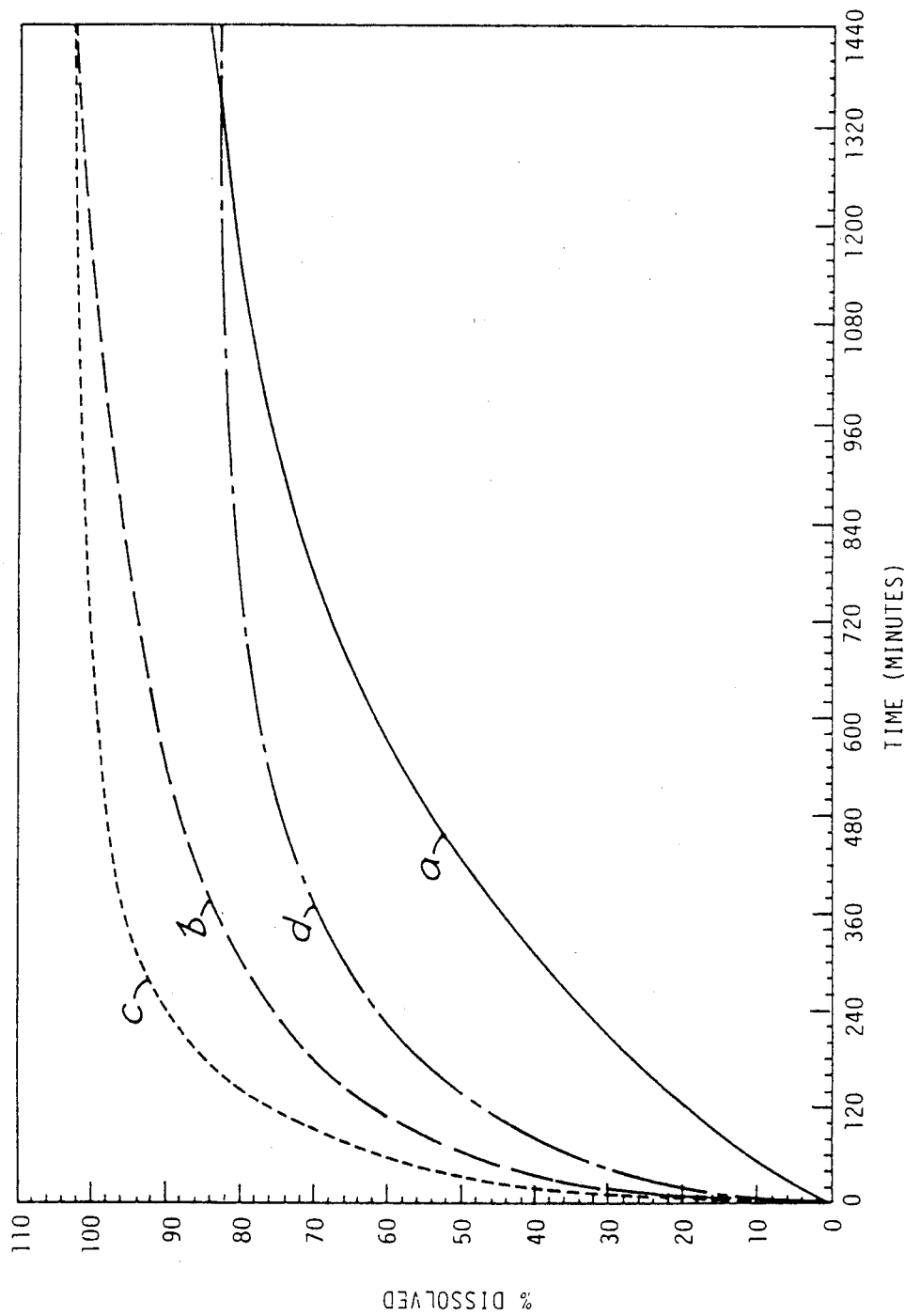
FIG. 8 illustrates comparison of the dissolution profiles of 3% coated Mefenamic acid beads free (a) and tabletted at three different pressures: <1.0 C.S. (b); 4.1 C.S. (c) and 8.1 C.S. (d)

Dissolution tests were performed on samples of the effervescent tablets of the present invention. For comparative purposes, tests were also performed on samples of the granules (or beads) containing mefenamic acid which were not compounded into tablets. The results are shown in FIG. 7. The dissolution profile for the effervescent tablets show a faster release than for the loose granules. However, the changes are not sufficient to destroy the sustained-release properties of the granules. The effect of different compaction pressures can be seen in FIG. 8. An increase in pressure to produce tablets of crushing strength 4 Kg from the minimum required to form a tablet of crushing strength 1 Kg, causes an increase in the release of drug. Higher pressure (producing tablets of crushing strength 8 Kg) reduces the release of drug compared with the other tablets.

Thus, sustained release profiles for mefenamic acid from effervescent tablets prepared according to the present invention can be prepared and profiles can be adjusted by controlling the compaction pressure.

EXAMPLE 8

A sustained-release formulation according to the present invention in the form of a water-dispersible tablet was prepared in the following manner:

(a) Mannitol Base

As for Example 2.

(b) Manufacture of Granules

| | |
|---|---|
| Mefenamic acid B.P. | 20.0 g |
| Tween 80 (4% solution) | 5.0 ml |
| Microcrystalline Cellulose U.S.N.F. | 1.1 g |
| Water | 8.0 ml |

The mefenamic acid was placed in a mortar and 5.0 ml of a 4% solution of Tween 80 was added in portions whilst the mixture was triturated with a pestle. The microcrystalline cellulose was then added and mixed in, followed by 1.0 ml portions of water until a slightly cohesive product was obtained. This product was formed into granules by forcing it into circular holes (2 mm diameter) in a perspex sheet (2 mm thickness). The granules were removed from the mould using a 2 mm cylindrical punch and were dried to constant weight at room temperature.

Preparation of Coating

As for Example 7.

Coating of the Granules

As for Example 7.

(c) Tablet Formation

The mannitol granules (176 mg) and coated granules containing mefenamic acid (88 mg), were compacted to form tablets 9 mm in diameter.

Crushing strength—As for Example 1.
Disintegration test—As for Example 1.
Dissolution test—As for Example 7.

(d) Dissolution Test Results

Figure 9:
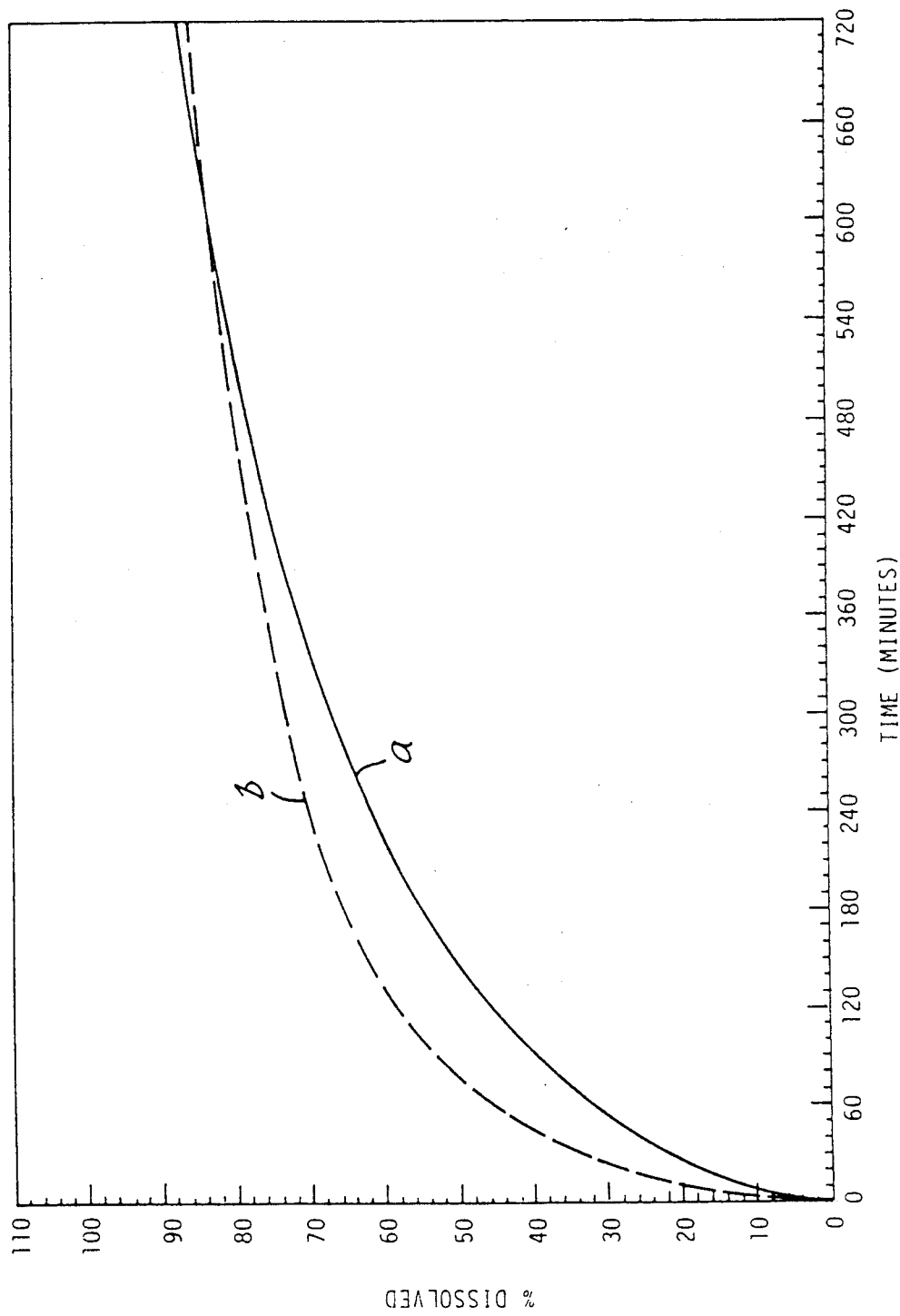
FIG. 9 illustrates dissolution curves for Mefenamic acid beads (a) and Mefanamic acid sustained-release dispersible tablets (b).

Tablets with crushing strengths of 4.0 Kg and disintegration time of 170 seconds were examined. Dissolution tests were performed on samples of the water-dispersible tablets of the present invention. For comparative purposes, tests were also performed on samples of the granules (or beads) containing mefenamic acid which were not compounded into tablets. The results are shown in FIG. 9. The dissolution profile for the dispersible tablet shows a slightly faster release of mefenamic acid than for the loose granules over the initial portion of the curve. After 6-7 hours, the two curves are almost identical. Thus, the sustained-release properties of the granules are essentially maintained in the dispersible tablet formulation.

We claim:

1. A sustained-release formulation of a pharmacologically active substance presented in the form of a tablet of sufficient granules to provide at least one predetermined dose of the pharmacologically active substance and effervescent or water-dispersible ingredients, each of said granules having a diameter of between about 0.5 and 2.5 mm and comprising:

a) a core comprising at least one pharmacologically active substance and at least one excipient;

b) a coating covering substantially the whole surface of the core and comprising about 100 parts of a water insoluble but water swellable neutral copolymer of ethyl acrylate and methyl methacrylate and from about 20 to 70 parts of a water soluble hydroxylated cellulose derivative, the weight of the coating being from about 2 to 25% of the weight of the core, and c) said tablet being adapted to substantially disintegrate into said granules upon being brought into contact with an aqueous liquid prior to being swallowed.

2. A formulation as claimed in claim 1, in which the granules provide sustained-release over a period of 12 hours, wherein the diameter of said granules is between 0.7 and 1.2 mm, the coating contains from 20 to 70 parts of the water soluble hydroxylated cellulose derivative, and the weight of the coating is between 2 and 15% of the weight of the core.

3. A formulation as claimed in claim 1, in which the granules provide sustained-release over a period of 24 hours, wherein the diameter of said granules is between 0.7 and 1.2 mm, the coating contains from 20 to 70 parts of the water soluble hydroxylated cellulose derivative, and the weight of the coating is between 5 and 25% of the weight of the core.

4. A formulation as claimed in claim 1, wherein the pharmacologically active substance is ibuprofen, nifedipine, naproxen or mefenamic acid.

5. A formulation as claimed in claim 1, wherein the hydroxylated cellulose derivative in the coating is hydroxypropylmethyl cellulose having a degree of substitution of 28 to 30% of methoxy groups and 7 to 12% of hydroxy groups.

6. A formulation as claimed in claim 1, wherein the effervescent ingredients comprise sodium bicarbonate and an organic carboxylic acid.

7. A formulation as claimed claim 1, wherein the water-dispersible ingredient comprises mannitol.

8. A method for preparing a sustained-release formulation of a pharmacologically active substance presented in the form of an effervescent or water-dispersible tablet of sufficient granules to provide at least one predetermined dose of the pharmacologically active substance and effervescent or water-dispersible ingredients, each of said granules having a diameter of between about 0.5 and 2.5 mm and comprising:

a) a core comprising at least one pharmacologically active substance and at least one excipient; and b) a coating covering substantially the whole surface of the core and comprising about 100 parts of a water insoluble but water swellable neutral copolymer of ethyl acrylate and methyl methacrylate and from about 20 to 70 parts of a water soluble hydroxylated cellulose derivative, the weight of the coating being from about 2 to 25% of the weight of the core, and c) said tablet being adapted to substantially disintegrate into said granules upon being brought into contact with an aqueous liquid prior to being swallowed, said method comprising:

i) mixing at least one pharmacologically active substance with at least one excipient;

ii) forming the mixture into core particles;

iii) forming a suspension comprising about 100 parts of a water insoluble but water swellable acrylic polymer and from about 20 to 70 parts of a water soluble hydroxylated cellulose derivative;

iv) coating the said core particles with the said suspension to form granules having a diameter of between about 0.5 and 2.5 mm, the weight of the coating being from about 2 to 25% of the weight of the core; and v) compressing a sufficient amount of the granules to provide at least one predetermined dose of the pharmacologically active substance, together with effervescent or water-dispersible ingredients, to form said effervescent or water-dispersible tablet.

9. A suspension of sustained-release granules in a non-toxic aqueous liquid formed by contacting such a liquid with a formulation as claimed in claim 1.

* * * * *

UNITED STATES PATENT AND TRADEMARK OFFICE
CERTIFICATE OF CORRECTION

PATENT NO. : 5,055,306　　　　　　　　　　　　　Page 1 of 2

DATED : October 8, 1991

INVENTOR(S) : Brian W. BARRY et al.

It is certified that error appears in the above-indentified patent and that said Letters Patent is hereby corrected as shown below:

Column 1, before line 11, insert --Background of the Invention--.

Column 2, after line 60, please insert -- SUMMARY OF THE INVENTION--.

Column 17, line 14, before "12 hours" please insert --about--.

Column 17, line 21, before "24 hours" please insert --about--.

UNITED STATES PATENT AND TRADEMARK OFFICE
CERTIFICATE OF CORRECTION

PATENT NO. : 5,055,306

DATED : October 8, 1991

INVENTOR(S) : Brian W. BARRY et al

It is certified that error appears in the above-indentified patent and that said Letters Patent is hereby corrected as shown below:

Column 18, after line 40, please add new claim 10 as follows

-- 10. A formulation as claimed in claim 1, wherein the aqueous liquid which contacts said tablet to cause substantial disintegration into said granules comprises saliva. --

Signed and Sealed this

Twenty-fifth Day of January, 1994

Attest:

BRUCE LEHMAN

*Attesting Officer*           *Commissioner of Patents and Trademarks*